United States Patent
Schutz et al.

(10) Patent No.: US 9,333,331 B2
(45) Date of Patent: May 10, 2016

(54) METHOD FOR IMPLANTING AN ACCESS PORT

(75) Inventors: Daniel Schutz, Aarwangen (CH);
Jean-Marc Guenat, Bienne (CH);
Adrian Auderset, Nidau (CH); Rudolf Hausler, Habstetten (CH); Felix Frey, Kriechenwil (CH); Anja Kruse, Wabern (CH); Andreas Arnold, Bern (CH);
Christof Stieger, St. Gallen (CH);
Marco Domenico Caversaccio, Liebefeld (CH)

(73) Assignee: Cendres+Metaux SA (CH)

( * ) Notice: Subject to any disclaimer, the term of this patent is extended or adjusted under 35 U.S.C. 154(b) by 352 days.

(21) Appl. No.: 13/291,817

(22) Filed: Nov. 8, 2011

(65) Prior Publication Data
US 2012/0116316 A1    May 10, 2012

Related U.S. Application Data

(60) Provisional application No. 61/411,018, filed on Nov. 8, 2010.

(51) Int. Cl.
*A61M 39/02*    (2006.01)

(52) U.S. Cl.
CPC ...... *A61M 39/0247* (2013.01); *A61M 2039/025* (2013.01); *A61M 2039/027* (2013.01); *A61M 2039/0261* (2013.01); *A61M 2039/0291* (2013.01)

(58) Field of Classification Search
CPC .............. A61M 1/3653; A61M 2039/025; A61M 2039/0261; A61M 2039/027; A61M 2039/0276; A61M 2039/0282; A61M 39/0247
USPC ........ 604/288.01–288.04, 175; 606/108, 237, 606/53
See application file for complete search history.

(56) References Cited

U.S. PATENT DOCUMENTS

| 4,108,173 A | * | 8/1978 | Slivenko et al. | 604/175 |
| 5,041,098 A | * | 8/1991 | Loiterman et al. | 604/175 |

(Continued)

FOREIGN PATENT DOCUMENTS

| EP | 0299547 | 1/1989 |
| WO | WO-81/03425 | 12/1981 |

(Continued)

OTHER PUBLICATIONS

Aperture—Merriam-Webster Dictionary. Accessed online Jun. 6, 2014.*

(Continued)

*Primary Examiner* — Kami A Bosworth
*Assistant Examiner* — Matthew A Engel
(74) *Attorney, Agent, or Firm* — Blank Rome LLP

(57) ABSTRACT

A transcutaneous access port to a user has a coupling member destined to be anchored in a bone of the user. A first valve system is removably connectable to the coupling member and a second valve system is removably connected to the first valve system. An internal conduit is connected at its proximal end to the access port and at its distal end to a vascular structure of the user. An external conduit is connected to the access port and to an extracorporeal device. A traversing cavity is formed in the bone at an implantation site of the user, passing the internal conduit. The internal conduit is routed through the traversing cavity to connect its distal end to the vascular structure of the user. The coupling member is anchored to the bone at the implantation site. The proximal end of the internal conduit is connected to the access port.

12 Claims, 7 Drawing Sheets

(56) References Cited

U.S. PATENT DOCUMENTS

| | | | |
|---|---|---|---|
| 5,332,398 A * | 7/1994 | Miller et al. | 604/175 |
| 5,350,360 A * | 9/1994 | Ensminger et al. | 604/288.03 |
| 5,527,277 A * | 6/1996 | Ensminger et al. | 604/116 |
| 5,990,382 A * | 11/1999 | Fox | 623/16.11 |
| 6,132,415 A * | 10/2000 | Finch et al. | 604/502 |
| 7,608,065 B2 * | 10/2009 | Glenn | 604/288.02 |
| 7,815,615 B2 * | 10/2010 | Jolly et al. | 604/288.02 |
| 7,833,204 B2 * | 11/2010 | Picha | 604/288.01 |
| 8,133,215 B2 * | 3/2012 | Gibson | 604/891.1 |
| 9,174,037 B2 * | 11/2015 | Schutz | A61M 39/0247 |
| 2005/0020873 A1 * | 1/2005 | Berrang | A61N 1/36032 600/25 |
| 2005/0159791 A1 * | 7/2005 | Daly | A61N 1/36032 607/57 |
| 2006/0047249 A1 | 3/2006 | Shubayev et al. | |
| 2006/0184143 A1 * | 8/2006 | Jolly et al. | 604/288.02 |
| 2007/0073250 A1 * | 3/2007 | Schneiter | 604/288.01 |
| 2007/0179456 A1 * | 8/2007 | Glenn | 604/288.01 |
| 2007/0255237 A1 * | 11/2007 | Lobl et al. | 604/288.01 |
| 2008/0200928 A1 * | 8/2008 | Savall Calvo | A61B 17/3403 606/130 |
| 2010/0094311 A1 * | 4/2010 | Jolly et al. | 606/129 |
| 2010/0255061 A1 * | 10/2010 | de Juan et al. | 424/427 |
| 2011/0034852 A1 * | 2/2011 | Hausler et al. | 604/6.16 |
| 2012/0157924 A1 * | 6/2012 | Schutz et al. | 604/175 |
| 2013/0030348 A1 * | 1/2013 | Lauer | 604/6.16 |
| 2013/0072847 A1 * | 3/2013 | Schutz | A61M 39/0247 604/6.16 |
| 2013/0165737 A1 * | 6/2013 | Van den Heuvel | A61N 1/36032 600/25 |
| 2013/0317517 A1 * | 11/2013 | Sterkers | A61B 17/3468 606/129 |
| 2014/0107400 A1 * | 4/2014 | Busca Grisoni | H04R 25/606 600/25 |
| 2014/0121447 A1 * | 5/2014 | Kasic | H04R 25/606 600/12 |

FOREIGN PATENT DOCUMENTS

| | | |
|---|---|---|
| WO | WO-2005/023336 A2 | 3/2005 |
| WO | WO-2007/051339 A1 | 5/2007 |
| WO | WO-2011/150978 A1 | 12/2011 |

OTHER PUBLICATIONS

Conduit—Merriam-Webster Dictionary. Accessed online Jun. 15, 2014.*

Channel—Merriam-Webster Dictionary. Accessed online Jun. 15, 2014.*

International Search Report for PCT/EP2010/057860 dated May 9, 2011.

* cited by examiner

METHOD FOR IMPLANTING AN ACCESS PORT

CROSS REFERENCE TO RELATED APPLICATION

This application claims the benefit of U.S. patent application Ser. No. 61/411,018 filed on Nov. 8, 2011, the disclosure of which is incorporated by reference herein in its entirety.

FIELD

The present disclosure relates to an implantable access port for removal and/or return of fluids to a user. The implantable access is usable for establishing temporary access to blood vessels, an organ, a body lumen or cavity or any combination thereof of a human or animal, for the purpose of hemodialysis, drug delivery, nutrition delivery, urinary catheterism or any other supply or removal of fluids. More particularly, the present disclosure relates o a method for implanting such access port.

BACKGROUND

Access to a user's lumen can be established by a variety of temporary and permanently implanted devices. However, despite several types of lumen access ports and devices proposed over recent years, body lumen access remains one of the most problematic areas in the treatment of users requiring long-term access. Most simply, temporary access can be provided by the direct percutaneous introduction of a needle through the user's skin and into a blood vessel. While such a direct approach is relatively straightforward and suitable for applications such as intravenous feeding, short term intravenous drug delivery and other applications which are limited in time, they are not suitable for hemodialysis and other extracorporeal procedures that must be repeated periodically and often for the user's lifetime.

In the present disclosure, unless otherwise specified, the expression "proximal" means on the side of the access port, and the expression "distal" means away from the access port.

SUMMARY

The present disclosure concerns a method for implanting a transcutaneous access port to a user comprising a coupling member destined to be anchored in a bone of the user, a first valve system removably connectable to the coupling member, a second valve system removably connected to the first valve system, an internal conduit adapted to be connected at its proximal end to the access port and at its distal end to a vascular structure of the user, and an external conduit adapted to be connected at its proximal end to the access port and at its distal end to an extracorporeal device; comprising: forming a traversing cavity in the bone at an implantation site of the user, the traversing cavity being adapted for passing the internal conduit; routing the internal conduit through the traversing cavity for connecting its distal end to the vascular structure of the user; anchoring the coupling member to the bone at the implantation site; connecting the proximal end of the internal conduit to the access port; and connecting the first and second valve system to the coupling member.

In an embodiment, the method further can comprise providing an anchoring area in the bone at the implantation site such that the coupling member contacts the bone on its base plate.

In another embodiment, the coupling member can comprise an outlet nozzle extending distally from the base plate, the traversing cavity being arranged such that the outlet nozzle is completely comprised within the traversing cavity; and wherein connecting the proximal end of the internal conduit comprises passing the internal conduit in the outlet nozzle.

In yet another embodiment, said bone can be the temporal or parietal bone.

In yet another embodiment, said routing the internal conduit can comprise the steps of:
performing a first incision in the skin such as to expose a part of the temporal and/or parietal bone;
providing a second incision on the user's neck;
puncturing and implanting the internal conduit in the internal jugular vein of the user; and
drawing the internal conduit through the traversing cavity.

In yet another embodiment, said drawing the internal conduit through the second incision can be performed using the Seldinger technique.

In yet another embodiment, the method can further comprise providing a second trench in the mastoid bone for guiding the internal conduit, the second trench being connected to the traversing cavity.

In yet another embodiment, the method can comprise the step of using a dummy conduit to control the dimensions of the second trench.

In yet another embodiment, the method can comprise the step of forming a first trench which is suitable for receiving at least part of the coupling member of the transcutaneous access port.

In yet another embodiment, the first trench can be formed using a milling caliber.

In yet another embodiment, the milling caliber can comprise a milling probe for controlling the dimension of the milled first trench.

In yet another embodiment, the second trench can extend between the first trench and towards the second incision.

In yet another embodiment, said providing a second trench can comprise performing a canal in the bone mastoid for guiding the internal conduit from the access port towards the caudal direction of the mastoid process.

In yet another embodiment, said traversing cavity can comprise the second trench and the first trench.

In yet another embodiment, said forming a traversing cavity can comprise connecting the first trench and the second trench by drilling in the first trench.

In yet another embodiment, the coupling member can comprise a fixation unit and wherein said fixing the coupling member to the bone is performed via the fixation unit.

In yet another embodiment, said fixation unit can comprise traversing holes and adapted to carry a screw to be anchored in the bone and wherein said fixing the coupling member to the bone is performed by fixing the screws in the bone.

In yet another embodiment, the method can further comprise the step of using a drilling caliber to provide a guide for drilling anchoring holes in a bone of a user, wherein the anchoring holes can be configured to cooperate with screws which are carried in traversing holes of the fixation unit.

In yet another embodiment, the method can comprise the step of arranging the drilling caliber such that one or more nub members on the drilling caliber cooperate with pilot holes provided in the user's bone, to fix the position of the drilling caliber.

In yet another embodiment, the method can further comprise the step of positioning at least part of the coupling member of the transcutaneous access port into a first trench.

In yet another embodiment, the method can further comprise the step of fixing the coupling member to a bone of the user using screws which engage the anchoring holes.

In yet another embodiment, said anchoring the coupling member can comprise implanting the coupling member in the bone such as to leave a bone portion between the base plate and the internal conduit.

In yet another embodiment, the method can further comprise the step of milling a trench in a bone of the user, to provide an anchor trench which is suitable to receive a protruding edge of the coupling member.

In yet another embodiment, the method can further comprise the step of drilling one or more pilot holes in a bone of the user.

In yet another embodiment, said providing an anchoring area comprises:
drilling one or more pilot holes in a bone of the user;
providing an anchor trench;
forming a first trench which is suitable for receiving at least part of the coupling member of the transcutaneous access port; and
drilling anchoring holes in the bone.

BRIEF DESCRIPTION OF THE DRAWINGS

The preferred embodiments will be better understood with the aid of the description of an embodiment given by way of example and illustrated by the figures, in which:

FIG. 3 illustrates a fixation unit of the coupling member according to an embodiment;

DETAILED DESCRIPTION OF THE PREFERRED EMBODIMENTS

Figure 1:
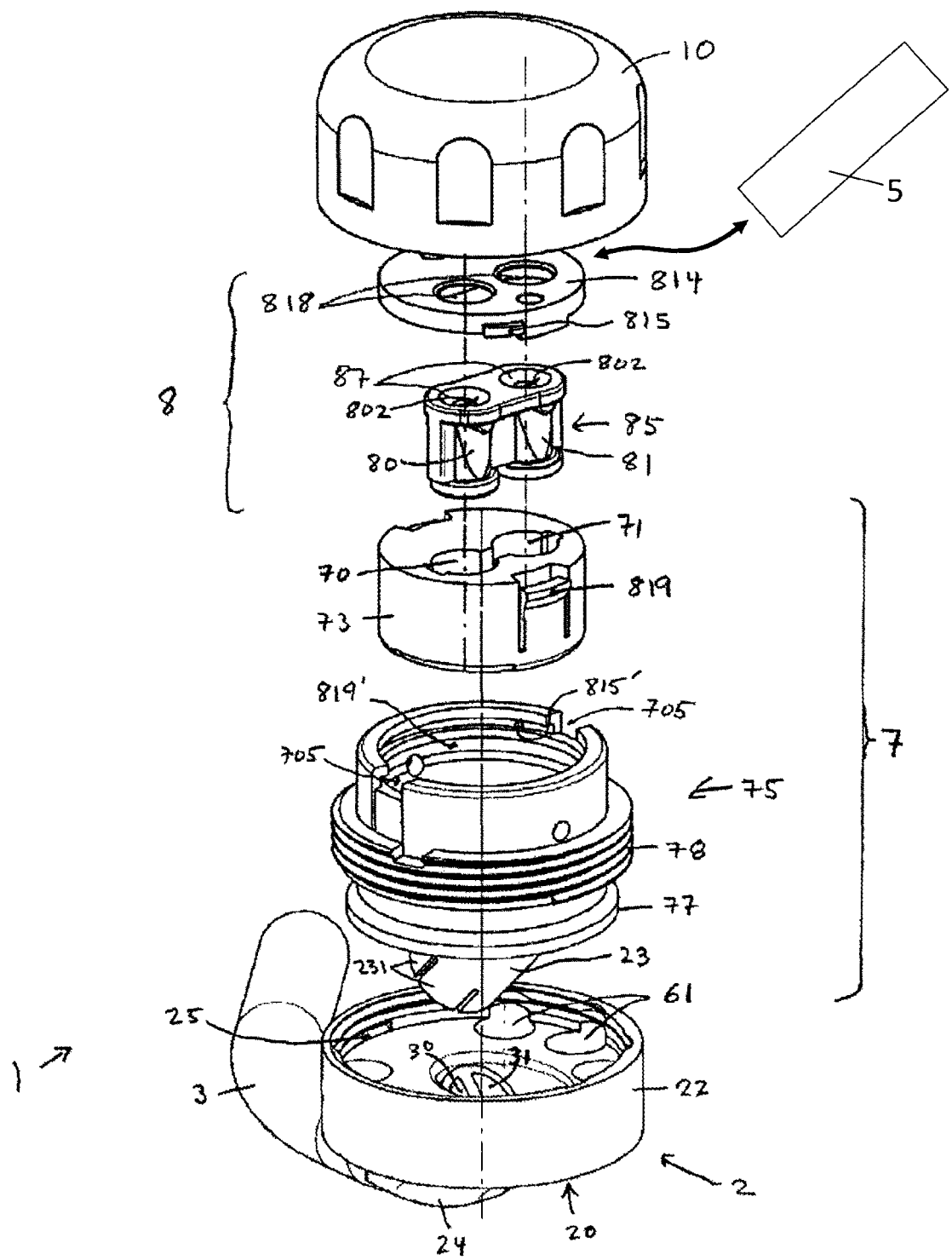
FIG. 1 shows an exploded view of an implantable access port comprising a coupling member according to an embodiment.

An Implantable access port 1 for removal and/or return of fluids to a user is shown in FIG. 1 according to an embodiment. The access port 1 comprises an internal conduit 3 adapted to be connected at its proximal end to the access port 1 and at its distal end to a vascular structure of the user; an external conduit 5 adapted to be connected at its proximal end to the access port 1 and at its distal end to an extracorporeal device; and a transcutaneous coupling member 2 destined to be anchored in a tissue of the user and comprising a first valve system 7 operable to be in an open or closed configuration to establish or block fluidic communication to and from the internal conduit 3. The coupling member 2 further comprises a second valve system 8 adapted to be removably connected to the first valve system 7 and operable to be in an open or closed configuration to establish or block fluidic communication to and from the external conduit 5, such as to establish fluid communication between the internal and external conduits 3, 5 when the first and second valve systems 7, 8 are connected and in the open configuration. More particularly, in the exploded view of FIG. 1, the transcutaneous coupling member 2 comprises a base plate 20 and a wall portion 22 and extending from the base plate 20. The wall portion 22 can have a substantially cylindrical shape or any other shape. Preferably, the wall portion has a tapered shape. An outlet nozzle 24 extends distally from the base plate 20 of the coupling member 2. A protective cap 10 can be fixed on the access port 1 when not in use, as shown in FIG. 1.

In the example of FIG. 1, the first valve system 7 comprises a cylindrical inner core 73 rotatably mounted within the coupling member 2. The inner core 73 comprises a valve conduit, here two passageways 70, 71, extending through it. When the first valve system 7 is in an open configuration, the inner core 73 is rotated in a position where the two passageways 70, 71 are aligned with the outlet nozzle 24, allowing fluid communication to and from the internal conduit 3. When the first valve system 7 is in a closed configuration, the inner core 73 is rotated in another position where the fluidic communication between the two passageways 70, 71 and the internal conduit 3 is blocked.

The distal end of the internal conduit 3 is destined to be connected to a vascular structure of the user, directly or via a lumen. In the embodiment of FIG. 1, the internal conduit 3 comprises two internal access lines 30, 31. For example, the internal conduit 3 can be a catheter for removal and/or return of fluids such as blood in a hemodialysis application. In the open configuration of the first valve system 7, the two passageways 70, 71 are respectively aligned with the two internal access lines 30, 31 of the internal conduit 3. In the closed configuration, the inner core 73 is rotated in a position where none of the two passageways 70, 71 are in fluidic communication with the internal access lines 30, 31.

More particularly in the embodiment of FIG. 1, the first valve system 7 further comprises a valve housing 75 in which the second cylindrical inner core 73 is rotatably mounted and destined to be removably fixed to the coupling member 2. Here, the inner core 73 is mounted into the valve housing 75 with two opposed locking lugs 819 engaging with a guiding flange 819'. The inner core 73 can be placed within (or removed from) the valve housing 75 by aligning the two locking lugs 819 with two corresponding recesses 705 provided at the first valve housing periphery.

Fixation of the valve housing 75 fixed to the coupling member 2 can be provided by screwing an upper thread 78 provided at the outer periphery of the valve housing 75, into a corresponding inner thread 25 provided in the inner side of the wall portion 22. The valve housing 75 can also comprise a lower flange 77 abutting against the base plate 20 when the valve housing 75 is being fixed to the coupling member 2. Here, a connection member 23 extending distally from the valve housing 75 is used for connecting the internal conduit 3 such that, when the valve housing 75 is fixed to the coupling member 2, the connection member 23 and the internal conduit 3 extend within the outlet nozzle 24. In this configuration, when the proximal end of the internal conduit 3 is connected to the access port 1 via the connection member 23, the internal conduit 3 is passed in the outlet nozzle 24.

In the embodiment of FIG. 1, the coupling member 2 further comprises a second valve system 8. Here, the second valve system 8 is a membrane valve comprising a first and a second sealing membrane 80, 81. The second valve system 8 can be removably connected to the first valve system 7. In the example of FIG. 1, the two sealing membranes 80, 81 are disposed in a second valve housing 85 having an outer shape adapted to fit tight within at least a portion of the first and second passageways 70, 71 of the inner core 73. Alternatively, the two sealing membranes 80, 81 and the second valve housing 85 can be made in a single piece. The sealing membranes 80, 81 can also be inserted directly within at least a portion of the passageways 70, 71. The second valve system 8 can be lockingly connected to the first valve system 7 using the clipping member 814. For example, the first and second sealing membranes 80, 81 can be press-fit into the passageways 70, 71. Here, the clipping member 814 can comprise locking members 815 destined to cooperate with a groove 815' such as to achieve a releasably-clipped engagement with the first valve housing 75. The clipping member 814 is provided with openings 818 allowing accessing the two sealing membranes 80, 81. The interface between the connected first and second valve systems 7, 8 can be made fluidly and air tight.

Further optional features of the access port 1 include the second valve system 8 being formed from a low profile second valve housing 85, and each sealing membrane 80, 81 being possibly provided with a preformed passage 802.

In an embodiment not represented, the first valve system 7 comprises a resilient valve conduit and a clamping device, the clamping device being adapted to apply a pressure on the resilient valve conduit, to collapse it and set the first valve system 7 in the closed configuration, and release the pressure allowing the resilient valve conduit to open, setting the first valve system 7 in the open configuration. This configuration is similar to the TEGO connectors and standard hose clip and pinch valves used in common dialysis equipments.

Other embodiment of the access port have been described in the not yet published pending patent application No. PCT/EP2010/057860 filed Jun. 4, 2010 by the present applicant, the disclosure of which is incorporated by reference herein in its entirety.

Figure 2:
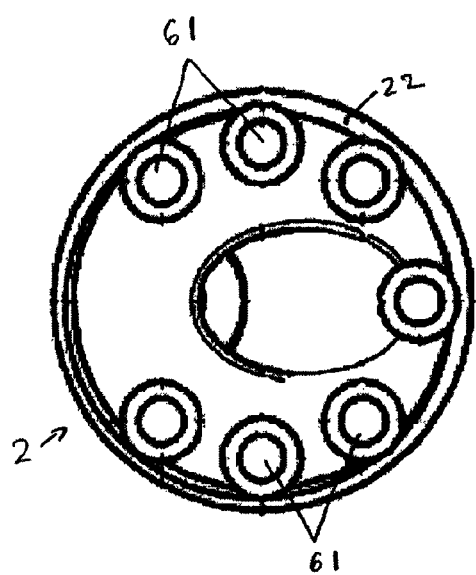
FIGS. 2 and 3 represents a top view of the coupling member including a fixation unit, according to an embodiment.

The coupling member 2 is adapted to be anchored to a bone of a user via a fixation unit. In the example of FIG. 1, the fixation unit comprises traversing holes 61 provided at the periphery of the base plate 20 and adapted to carry a screw (not shown) for anchoring the coupling member 2 by means of screws. A top view of the coupling member 2 is represented in FIG. 2 where the holes 61 and the outlet nozzle 24 can be easily seen.

Figure 3:
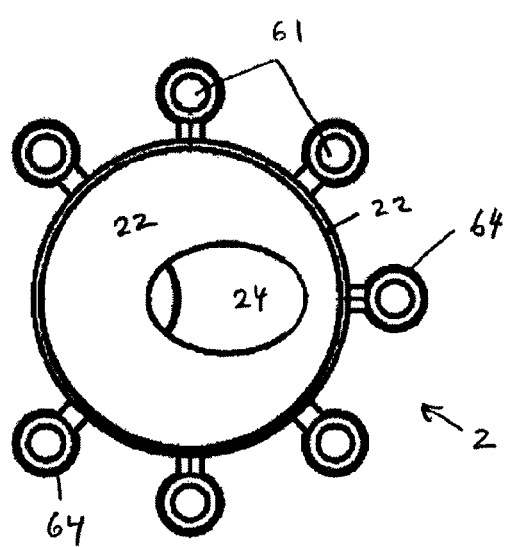
Figure 4:
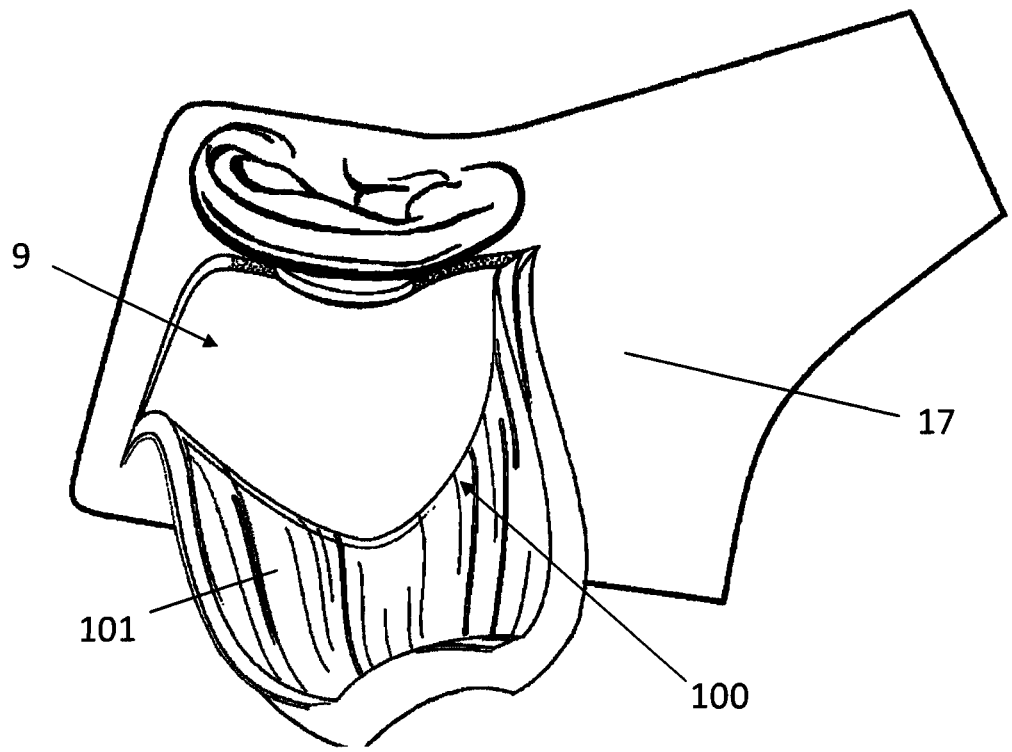
FIG. 4 represents performing an incision in the skin of a user, according to an embodiment.

In another embodiment shown in FIG. 3, the fixation unit comprises a number of arms 64 attached to the coupling member 2 and provided with holes 61 for carrying a screw (not shown), for anchoring the coupling member 2 by means of screws. In this latter configuration, the number of arms 64 can vary, being typically three or more, depending on the size and intended placing. The arms 64 can be pivotal and inclinable to admit maximum of adaptation to the substrate to which they shall be screwed. Alternatively, the fixation unit can also comprise pins, wires, non-absorbable threads, cement or any other suitable fixation means.

In a preferred embodiment, the coupling member 2 is destined be anchored to a bone such as the hip, clavicle, sternum or any other section of the skeleton. More preferably, the coupling member 2 is destined to be permanently anchored to the temporal or parietal bone 9.

A method for implanting the transcutaneous access port 1 to a user is represented schematically in FIGS. 4 to 10, according to an embodiment. The user's may be moved into a suitable position before the process for implantation begins;
for example if the transcutaneous access port 1 is to be implanted in a temporal or parietal bone of a user, then the head of the user may be positioned in a dorsal position; and depending on where the transcutaneous access port 1 is to be implanted, shaving of hair on the user's body may be required. Other standard surgical steps may also be employed such as sterilizing the region of the user's body where the transcutaneous access port 1 is to be implanted and sketching guide lines for incisions on the user's body e.g sketching guide lines for a retroauricular incision S-cut. The method for implanting the transcutaneous access port 1 to a user can comprise the steps of:

forming a traversing cavity 90, 92 in the bone at an implantation site of the user, the traversing cavity 90, 92 being adapted for passing the internal conduit 3;

anchoring the coupling member 2 to the bone 9 at the implantation site;

routing the internal conduit 3 through the traversing cavity 90, 92 for connecting its distal end to the vascular structure of the user;

connecting the proximal end of the internal conduit 3 to the access port 1.

In an embodiment, said fixing the coupling member 2 is performed in the temporal or parietal bone 9.

In another embodiment, the method further comprises one or several steps of preparing the implantation site comprising: performing a first retroauricular incision 100 in the skin 17, and moving the cut skin, i.e. skin flap 101, in order to expose the mastoid bone and a part of the temporal and/or parietal bone 9 (FIG. 4), prior to said forming a traversing-cavity 90, 92; and providing pilot holes, e.g. two pilot holes, for the implantation screws and fixation of the coupling member 2.

Figure 5A:
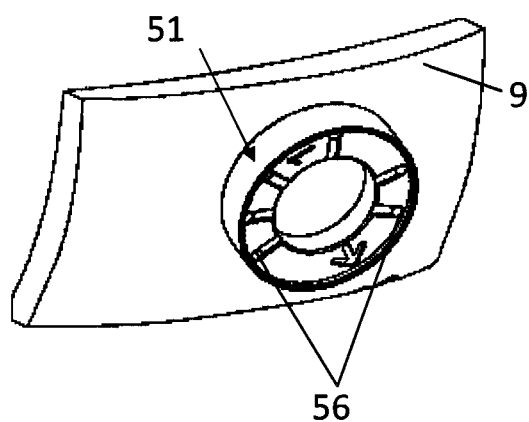
FIGS. 5a to 5e illustrate method for implanting the access port to the user, according to an embodiment.
Figure 5B:
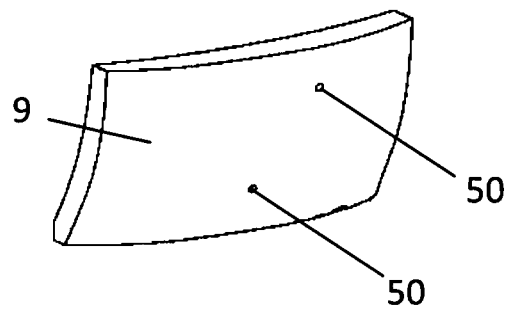

As shown in FIG. 5a, a drilling caliber 51 may be used to facilitate the drilling of pilot holes 50 in an accurate position on the bone 9 of the user. The drilling caliber 51 is an element which comprises a one or more drilling guide holes 56 which define the positions for one or more holes e.g. pilot holes. The drilling caliber 51 is positioned, in a selected orientation, on the bone 9 of the user before drilling of the pilot holes 50 takes place. Once the drilling caliber 51 is in place the pilot holes 50 may be drilled in the user's bone 9 by drilling through the guide holes 56 provided in the drilling caliber 51. The drilling caliber 51 will enable a surgeon to drill accurately positioned pilot holes 50; the pilot holes will be positioned accurately relative to one another and the pilot holes 50 will be positioned at the correct position on the bone 9 of the user. FIG. 5a shows the drilling caliber 51 positioned on the temporal or parietal bone 9 of the patent and arranged so that the drilling caliber 51 is pointing towards the mastoid process tip of the user. FIG. 5b shows the bone with two drilled pilot holes 50.

Figure 5C:
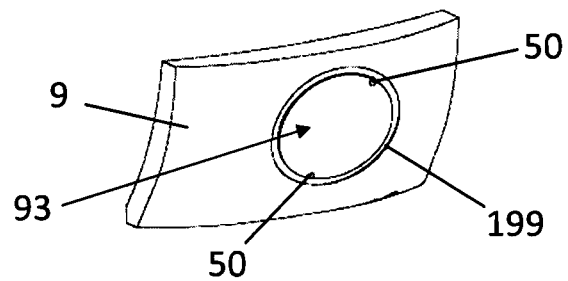

In an embodiment shown in FIG. 5c, preparing the implantation site further comprises providing an anchor trench 199. The anchor trench 199 can be formed by using a bone cutter, where the latter can be guided, using pilot holes 50, such as to facilitate accurate milling and positioning of the anchor-trench 199. The anchor trench 199 is a trench which is suitable for receiving an anchoring means of the coupling member 2. For example, the anchor trench 199 can be configured for receiving a protruding edge (not shown) of the coupling member 2. In this case, the anchor trench 199 can be configured conformal with the protruding edge of the coupling member 2. Optionally, the depth of the anchor trench 199 can be controlled with the drilling caliber 51. The method can further comprise the step of providing a substantially flat anchoring area 93 in the bone 9 at the implantation site such that the coupling member 2 contacts the bone 9 on its lower surface and along its periphery. In FIG. 5b, such anchoring area 93 is represented as having the same size, or surface area, as the one of the base plate 20, e.g., corresponding to the surface within the anchor trench 199. Preferably, the anchoring area 93 has an anchoring surface shape that is conformal with the base plate 20.

Figure 5D:
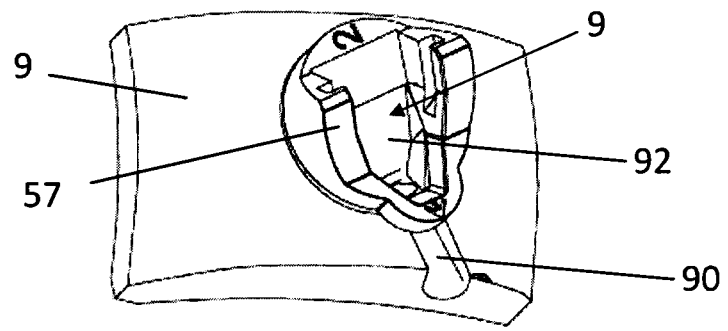
Figure 5E:
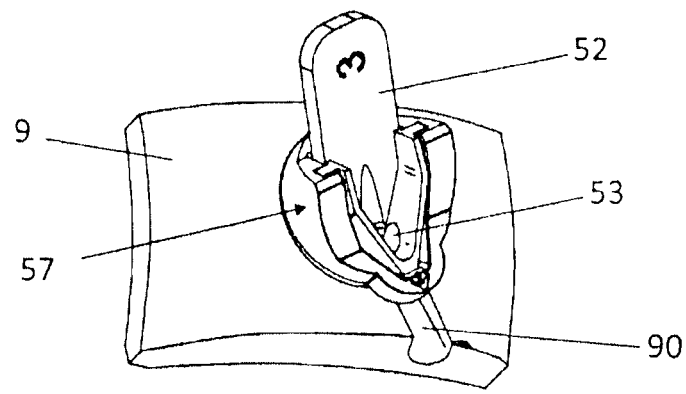
Figure 7:
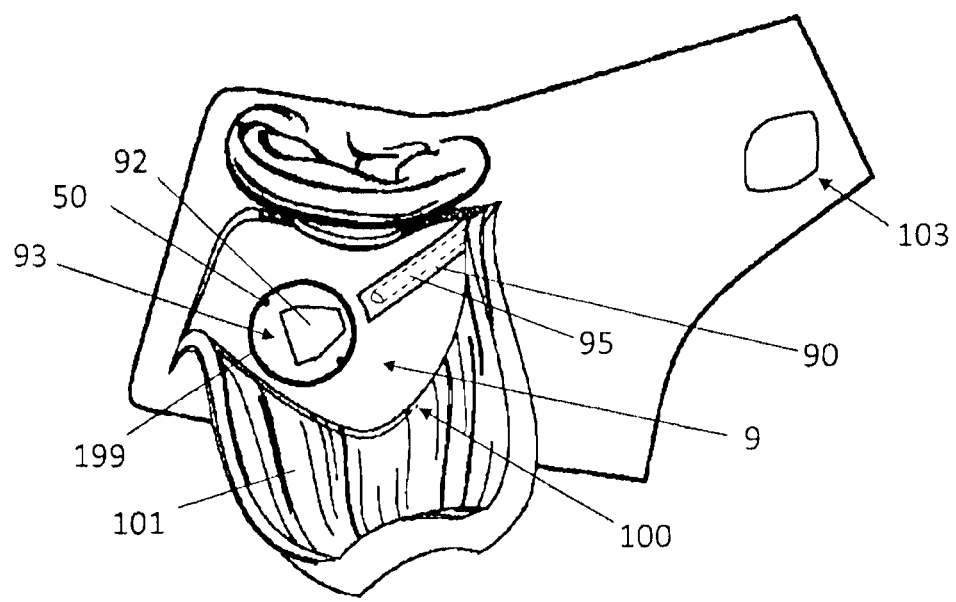
FIG. 7 represents anchoring area with anchor, first and second trench and anchoring holes, according to an embodiment.

Once the anchor trench 199 is milled, a milling caliber 57 can be secured to the user's bone 9, as shown in FIGS. 5d and 5e. The milling caliber 57 can comprise nubs members (not shown) suitable for cooperating with pilot holes 50 to removably fix the position of the milling caliber 57. The milling caliber 57is useful as a guide to ensure that any milled trenches and cavities etc. will be of suitable configurations for cooperating with the eventually implanted coupling member 2In an embodiment, a first trench 92 (see FIGS. 5d and 10) is milled within the milling caliber 57 (see FIG. 5d). The dimensions of the milled first trench 92 can then be controlled using a milling probe 52 that can be inserted into the milling caliber 57. FIG. 7 illustrates the exposed bone 9 with the anchor trench 199 and milled first trench 92.

The method can also comprise providing a second trench 90 (see FIG. 7) in the bone 9 for guiding the internal conduit 3. The second trench 90 may be provided by drilling. The dimensions e.g width, of the second trench 90 may be controlled using a dummy conduit 95. The second trench 90 can be a canal in the bone 9 for guiding the internal conduit 3 from the access port 1 towards the caudal direction of the mastoid process. The second trench 90 extends between the first trench 92 and towards a second incision 103 on the neck. Passing the internal conduit 3 in the second trench 90 allows for stabilizing it against possible displacements of the internal conduit 3, for example when manipulating the access port 1 or due to movements of the user.

A further method step can comprise connecting the first trench 92 to the second trench 90 to form the traversing cavity 90, 92. This can be performed by drilling in the bottom of the first trench 92. Adequate size and position of the drilling can be achieved by securing again the milling caliber 57 to the user's bone 9, and inserting the milling probe 52 into the milling caliber 57. In the example of FIG. 5e, the milling caliber 57 comprises a cavity guide 53 that can be used to guide the drilling operation. The drilling operation can be such as to connect the first trench 92 to the second trench 90 and thus provide the traversing cavity 90, 92. Alternatively, connecting the first trench 92 to the second trench 90 can comprise a further drilling operation performed at the bottom of the second trench 90.

Figure 8:
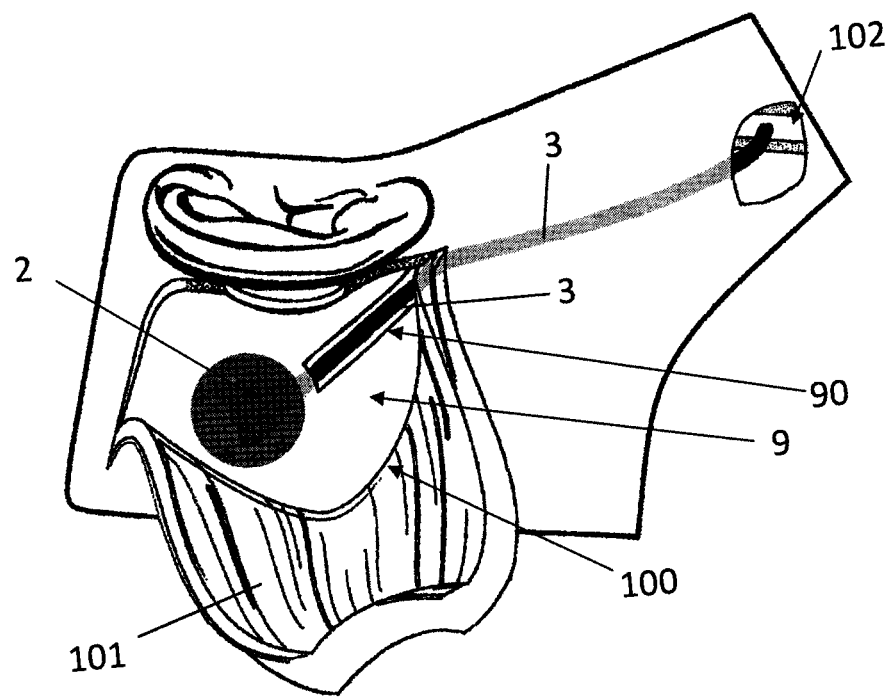
FIG. 8 shows coupling member anchored in the user's bone, according to an embodiment.

Once the trenches 90, 92 have been drilled in the user's bone 9, anchoring holes 62 are drilled in the user's bone, as illustrated in FIG. 8. The anchoring holes 62 will be in the same relative positioning as the relative positioning of the traversing holes 61 provided at the periphery of the base plate 20. The anchoring holes 62 will be configured to receive screws or fasteners (not shown), which pass through the traversing holes 61 of the base plate 20, so that the coupling member 2 can be anchored to the user's bone 9. The drilling caliber 51 will comprises a one or more drilling guide holes 56 which define the positions for one or more anchoring holes 62. The drilling caliber 51 can further comprise nubs (nor shown) adapted to cooperate with the pilot holes 50. To drill the one or more anchoring holes 62, the drilling caliber 51 is arranged such that the nub members cooperate with pilot holes 50 in the bone 9 of the patent, to removably fix the position of the drilling caliber 51. Once the position of the drilling caliber 51 is fixed, the surgeon may drill the user's bone 9 at the one or more drilling guide holes 56 of the drilling caliber 51 to form anchoring holes 62 in the bone 9. The drilling caliber 51 will ensure that the positioning of the drilled anchoring holes 62 is accurate. The pilot holes 50 with which the nub members cooperate, may also be used as anchoring holes 62 once the drilling caliber 51 has been removed.

Figure 9:
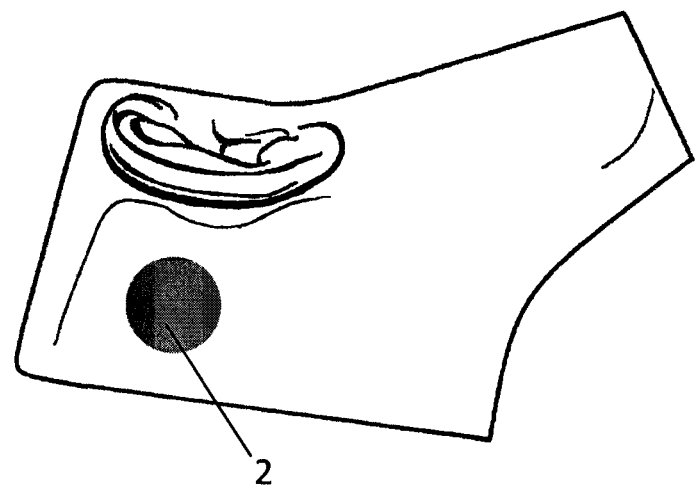
FIG. 9 illustrates the implanted access port, according to an embodiment.

With the anchoring holes 62 drilled, the coupling member 2 is inserted into the anchoring area 93 and secured by screws or fasteners (not shown) which pass through the traversing holes 61 of the base plate 20, into the anchoring holes 62, as shown in FIGS. 8 and 9.

Figure 6:
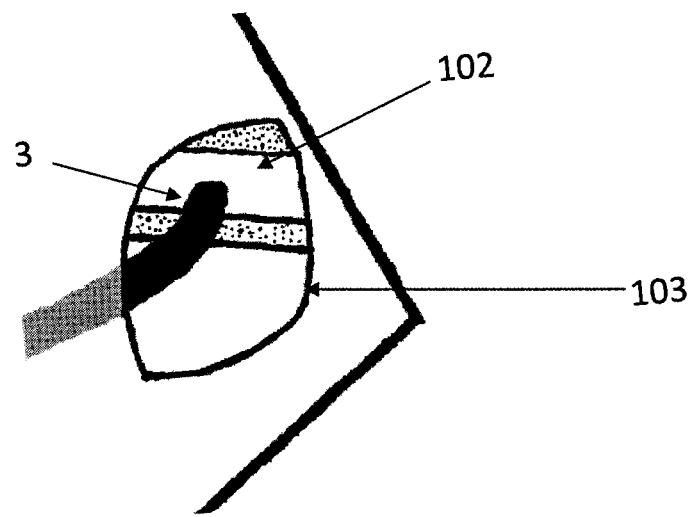
FIG. 6 represents performing a second incision at the user's neck with entrance of an internal conduit in a vascular structure of the user, according to an embodiment.

In an embodiment illustrated in FIGS. 6 and 7, routing the internal conduit 3 comprises the steps of providing a second incision 103 on the user neck (cervicotomy); puncturing and implanting the internal conduit 3 in the internal jugular vein; and drawing the internal conduit 3 through the first trench 92. Here, drawing the internal conduit 3 through the incision on the neck is performed using the Seldinger technique or any other suitable technique. During drawing, the position of the internal conduit 3 can be controlled visually, for example, using a C-shaped x-ray device (C-bogen device) or any other suitable technique.

After drawing the internal conduit 3 and prior connecting the proximal end of the internal conduit 3 to the access port 1, the internal conduit 3 can be cut to a predetermined length such that it extends along a minimal length from the vascular structure 102, through the bone 9, and outside the cavity, when the proximal end of the internal conduit 3 is attached to the access port 1 and the latter is fixed to the bone 9.

Connecting the proximal end of the internal conduit 3 to the access port 1 can then be performed by connecting the internal conduit 3 to the first valve system 7, for example via the connection member 23, as described above. Alternatively, the internal conduit 3 can be connected to the second valve system 8.

After the internal conduit 3 is connected to the first or second valve system 7, 8, the valve systems 7, 8 can be mounted on the coupling member being fixed to the bone 9. In an embodiment, the access port 1 can be assembled by passing the internal conduit 3 through the outlet nozzle 24 of the coupling member 2, connecting the internal conduit 3 to the connection member 23 of the first valve system 7, fitting the sealing membranes 80, 81 to first valve system 7, for example within the passageways 70, 71, and fixing the first valve system 7, connected to the second valve system 8, to the coupling member 2. Assembling the access port 1 can further comprise the step of mounting the inner core 73 in the valve housing 75.

Figure 10:
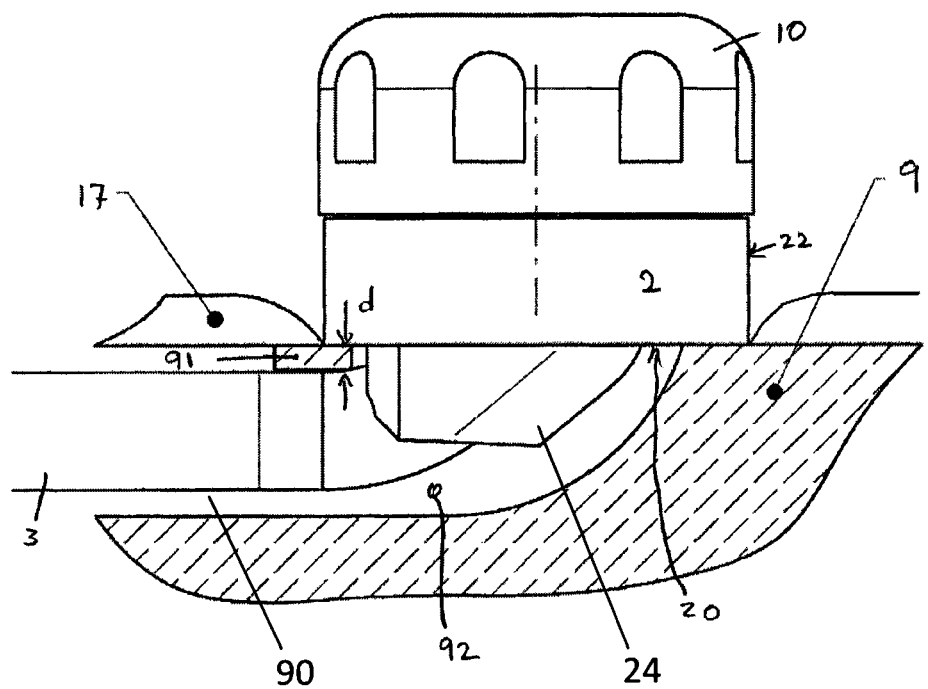
FIG. 10 represents the implanted access port, according to another embodiment.

In FIG. 10, the coupling member 2 is represented implanted in the bone 9 with the outlet nozzle 24 being fully buried in the bone 9. An internal conduit 3 extends through the outlet nozzle 24 and in the first trench 92 provided in the bone 9. The internal conduit 3 extends from the outlet nozzle 24 at a distance d underneath the base plate 20 such as to leave a bone portion 91 between the base plate 20 and the internal conduit 3. In this configuration, bone 9 can contact the coupling member 2 along its whole periphery. The skin 17 can then be in contact only with the bone 9 and possible passages or grooves between the skin 17 and the first coupling member 2 are avoided, thus decreasing the risk of infection. The spacing d can be typically greater than 1 mm to allow for the bone portion 91 between the base plate 20 and the internal conduit 3 to have a thickness such as to be structurally solid enough. Here, the internal conduit 3 extends through an outlet nozzle 24 extending below the coupling member 2, and the first trench 92 is arranged such that the outlet nozzle 24 is completely comprised within said first trench 92.

After mounting, the access port 1 can be tested, for example by flushing of access port 1 and set the valve systems 7, 8 in the closed configuration. In the case the access port 1 is functioning correctly, subcutaneous border of the wound can be moved away from the coupling member2, the wound be disinfected, and wound bandage can be provided covering the access port 1, such to allow the implanted access port 1 to heal.

The modular construction of the access port 1 described above allows for removing the internal conduit 3 without the need to remove the first coupling member 2, i.e., removing and fixing the coupling member in the bone. Moreover, the second valve system 8 is arranged such that it must be replaced periodically. In this case, the first valve system 2 can be used to sealingly close the internal conduit 3 can be closed against entering of air and/or exit of blood. The access port 1 is arranged such that the direction of the arterial and venous lumens can be changed upon closing the first valve system 7.

REFERENCE NUMBERS 1 access port
2 coupling member
3 internal conduit
7 first valve system
8 second valve system
9 bone
10 protective cap
17 skin
20 base plate
22 wall portion
23 connection member
24 outlet nozzle
25 inner thread
30, 31 internal access lines
50 pilot holes
51 drilling caliber
52 milling probe
53 cavity guide
56 guide holes
57 milling caliber
58 bone cutter
61 traversing holes
62 anchoring holes
64 arms
70, 71 passageways
73 cylindrical inner core
75 valve housing
77 lower flange
78 upper thread
705 recesses
80,81 sealing membranes
85 second valve housing
802 preformed passage
814 clipping member
815 locking members
815' groove
818 openings
819 locking lugs
819' guiding flange
90 second trench
91 bone portion
92 first trench
93 anchoring area
100 first incision
101 skin flap
102 vascular structure
103 second incision
199 anchor trench
d spacing

The invention claimed is:

1. A method for implanting a transcutaneous access port to a user, the transcutaneous access port having a coupling member destined to be anchored in a bone of the user, the coupling member comprises a base plate and an outlet nozzle extending distally from the base plate, a first valve system removably connectable to the coupling member, wherein the first valve system is configured such that it can be opened or closed by mechanical rotation of a component of the first valve system, a second valve system removably connected to the first valve system, an internal conduit adapted to be connected at its proximal end to the access port and at its distal end to a vascular structure of the user, and an external conduit adapted to be connected at its proximal end to the access port and at its distal end to an extracorporeal device; comprising:

forming a traversing cavity in the bone at an implantation site of the user, the traversing cavity being adapted for passing the internal conduit, the traversing cavity being further arranged such that the outlet nozzle is completely comprised within the traversing cavity;

routing the internal conduit through the traversing cavity for connecting its distal end to the vascular structure of the user;

anchoring the coupling member to the bone at the implantation site; and connecting the proximal end of the internal conduit to the access port by passing the internal conduit in the outlet nozzle.

2. A method for implanting a transcutaneous access port to a user, the transcutaneous access port having a coupling member destined to be anchored in a bone of the user, a first valve system removably connectable to the coupling member, a second valve system removably connected to the first valve system, an internal conduit adapted to be connected at its proximal end to the access port and at its distal end to a vascular structure of the user, and an external conduit adapted to be connected at its proximal end to the access port and at its distal end to an extracorporeal device; comprising:

forming a traversing cavity in the bone at an implantation site of the user, the traversing cavity being adapted for passing the internal conduit;

routing the internal conduit through the traversing cavity for connecting its distal end to the vascular structure of the user;

anchoring the coupling member to the bone at the implantation site; and connecting the proximal end of the internal conduit to the access port;

and wherein the coupling member comprises a base plate and an outlet nozzle extending distally from the base plate, the traversing cavity being arranged such that the outlet nozzle is completely comprised within the traversing cavity; and wherein connecting the proximal end of the internal conduit comprises passing the internal conduit in the outlet nozzle.

3. A method for implanting a transcutaneous access port to a user, the transcutaneous access port having, a coupling member destined to be anchored in a bone of the user, the coupling member having a base plate and an outlet nozzle extending distally from the base plate, a first valve system removably connectable to the coupling member, a second valve system removably connected to the first valve system, wherein the first and second valve systems are arranged to remain substantially extracorporeal when the access port is implanted, a structure which defines an internal conduit, wherein said internal conduit is adapted to be physically connected at its proximal end to the access port and at its distal end to a vascular structure of the user, and wherein the second valve system is configured to be connected with an external conduit structure that is adapted to be physically connected at its proximal end to the access port and at its distal end to an extracorporeal device, the method comprising:

forming a traversing cavity in the bone at an implantation site of the user, the traversing cavity being adapted for passing the internal conduit, the traversing cavity being further arranged such that the outlet nozzle is completely comprised within the traversing cavity;

routing the internal conduit through the traversing cavity for connecting its distal end to the vascular structure of the user;

anchoring the coupling member to the bone at the implantation site; and connecting the proximal end of the internal conduit to the access port by passing the internal conduit in the outlet nozzle.

4. The method according to claim 3, wherein the coupling member comprises a base plate and wherein the method further comprises providing an anchoring area in the bone at the implantation site such that the coupling member contacts the bone on the base plate.

5. The method according to claim 4, wherein said anchoring the coupling member comprises implanting the coupling member in the bone such as to leave a portion of bone between the base plate and the internal conduit.

6. The method according to claim 3, wherein forming the traversing cavity comprises providing a trench in a mastoid bone for guiding the internal conduit.

7. The method according to claim 6, further comprising using a dummy conduit to control the dimensions of the trench.

8. The method according to claim 6, wherein said providing the trench comprises forming a canal in the mastoid bone for guiding the internal conduit from the access port towards a caudal direction of a mastoid process.

9. The method according to claim 3, wherein forming the traversing cavity comprises forming a first trench which is suitable for receiving at least part of the coupling member of the transcutaneous access port.

10. The method according to claim 9, wherein forming the traversing cavity further comprises forming a second trench, wherein the second trench extends between the first trench and towards an incision.

11. The method according to claim 3, wherein said traversing cavity comprises a second trench and a first trench.

12. The method according to claim 11, wherein said forming a traversing cavity comprises connecting the first trench and the second trench by drilling in the first trench.

\* \* \* \* \*